(12) United States Patent
Toews et al.

(10) Patent No.: US 12,239,453 B2
(45) Date of Patent: Mar. 4, 2025

(54) SYSTEM AND METHOD FOR AUTOMATIC PERSONALIZED ASSESSMENT OF HUMAN BODY SURFACE CONDITIONS

(71) Applicant: Little Angel Medical Inc., Pointe-Claire (CA)

(72) Inventors: Matthew Toews, Pointe-Claire (CA); James Lee, Pointe-Claire (CA); Mohsen BenLazreg, Trois-Rivieres (CA)

(73) Assignee: LITTLE ANGEL MEDICAL INC., Pointe-Claire (CA)

( * ) Notice: Subject to any disclaimer, the term of this patent is extended or adjusted under 35 U.S.C. 154(b) by 107 days.

(21) Appl. No.: 18/102,253

(22) Filed: Jan. 27, 2023

(65) Prior Publication Data
US 2023/0284968 A1 Sep. 14, 2023

Related U.S. Application Data

(60) Provisional application No. 63/308,188, filed on Feb. 9, 2022.

(51) Int. Cl.
*A61B 5/00* (2006.01)

(52) U.S. Cl.
CPC ............ *A61B 5/445* (2013.01); *A61B 5/0077* (2013.01); *A61B 5/6898* (2013.01); *A61B 2503/04* (2013.01)

(58) Field of Classification Search
CPC ..... A61B 5/445; A61B 5/0077; A61B 5/6898; A61B 2503/04; A61B 1/227; A61B 5/444; A61B 5/7267
See application file for complete search history.

(56) References Cited

U.S. PATENT DOCUMENTS

| | | | | |
|---|---|---|---|---|
| 2014/0316235 | A1* | 10/2014 | Davis | G16H 50/20 600/407 |
| 2017/0367580 | A1* | 12/2017 | DiMaio | A61B 5/445 |

(Continued)

*Primary Examiner* — Baisakhi Roy
*Assistant Examiner* — Kaitlyn E Sebastian

(57) ABSTRACT

A system and method for personalized diagnosis of human body surface conditions from images acquired from a mobile camera device. In an embodiment, the system and method is used to diagnose skin, throat and ear conditions from photographs. A system and method are provided for data acquisition based on visual target overlays that minimize image variability due to camera pose at locations of interest over the body surface, including a method for selecting a key image frame from an acquired input video. The method and apparatus may involve the use of a processor circuit, for example an application server, for automatically updating a visual map of the human body with image data. A hierarchical classification system is proposed based on generic deep convolution neural network (CNN) classifiers that are trained to predict primary and secondary diagnoses from labelled training images. Healthy input data are used to model the CNN classifier output variability in terms of a normal model specific to individual subjects and body surface locations of interest. Personalized diagnosis is achieved by comparing CNN classifier outputs from new image data acquired from a subject with a potentially abnormal condition to the healthy normal model for the same specific subject and location of interest.

9 Claims, 8 Drawing Sheets

(56) References Cited

U.S. PATENT DOCUMENTS

| | | | |
|---|---|---|---|
| 2020/0117901 A1* | 4/2020 | McClernon | G08B 31/00 |
| 2022/0051409 A1* | 2/2022 | Maclellan | G16H 50/70 |
| 2024/0065554 A1* | 2/2024 | Serval | G06V 20/20 |

* cited by examiner

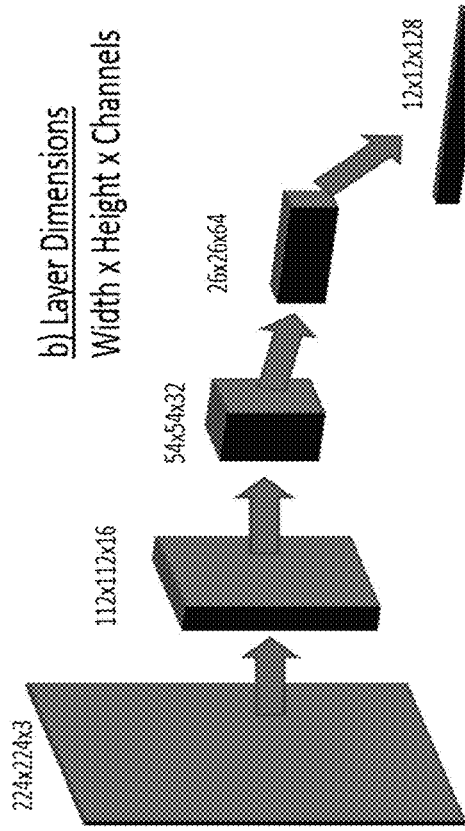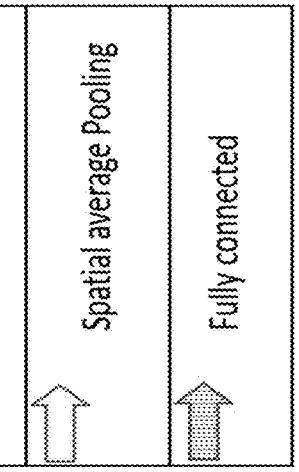
FIG. 6 a) Skin

| Layer (type) | Output Shape | Param # |
|---|---|---|
| conv2d_6 (Conv2D) | (None, 222, 222, 16) | 448 |
| activation_5 (Activation) | (None, 222, 222, 16) | 0 |
| max_pooling2d_6 (MaxPooling2 | (None, 111, 111, 16) | 0 |
| conv2d_7 (Conv2D) | (None, 109, 109, 32) | 4640 |
| activation_6 (Activation) | (None, 109, 109, 32) | 0 |
| max_pooling2d_7 (MaxPooling2 | (None, 54, 54, 32) | 0 |
| conv2d_8 (Conv2D) | (None, 52, 52, 64) | 18496 |
| activation_7 (Activation) | (None, 52, 52, 64) | 0 |
| max_pooling2d_8 (MaxPooling2 | (None, 26, 26, 64) | 0 |
| conv2d_9 (Conv2D) | (None, 24, 24, 64) | 36928 |
| activation_8 (Activation) | (None, 24, 24, 64) | 0 |
| max_pooling2d_9 (MaxPooling2 | (None, 12, 12, 64) | 0 |
| conv2d_10 (Conv2D) | (None, 10, 10, 128) | 73856 |
| max_pooling2d_10 (MaxPooling | (None, 5, 5, 128) | 0 |
| global_average_pooling2d_2 ( | (None, 128) | 0 |
| dense_2 (Dense) | (None, ) | 903 |

Total params: 135,271 b) Throat

| Layer (type) | Output Shape | Param # |
|---|---|---|
| conv2d_26 (Conv2D) | (None, 222, 222, 16) | 448 |
| activation_21 (Activation) | (None, 222, 222, 16) | 0 |
| max_pooling2d_26 (MaxPooling | (None, 111, 111, 16) | 0 |
| conv2d_27 (Conv2D) | (None, 109, 109, 32) | 4640 |
| activation_22 (Activation) | (None, 109, 109, 32) | 0 |
| max_pooling2d_27 (MaxPooling | (None, 54, 54, 32) | 0 |
| conv2d_28 (Conv2D) | (None, 52, 52, 64) | 18496 |
| activation_23 (Activation) | (None, 52, 52, 64) | 0 |
| max_pooling2d_28 (MaxPooling | (None, 26, 26, 64) | 0 |
| conv2d_29 (Conv2D) | (None, 24, 24, 128) | 73856 |
| activation_24 (Activation) | (None, 24, 24, 128) | 0 |
| max_pooling2d_29 (MaxPooling | (None, 12, 12, 128) | 0 |
| conv2d_30 (Conv2D) | (None, 10, 10, 256) | 295168 |
| max_pooling2d_30 (MaxPooling | (None, 5, 5, 256) | 0 |
| global_average_pooling2d_5 ( | (None, 256) | 0 |
| dense_8 (Dense) | (None, 2) | 514 |

Total params: 393,122 c) Ear

| Layer (type) | Output Shape | Param # |
|---|---|---|
| conv2d_26 (Conv2D) | (None, 222, 222, 16) | 448 |
| activation_21 (Activation) | (None, 222, 222, 16) | 0 |
| max_pooling2d_26 (MaxPooling | (None, 111, 111, 16) | 0 |
| conv2d_27 (Conv2D) | (None, 109, 109, 32) | 4640 |
| activation_22 (Activation) | (None, 109, 109, 32) | 0 |
| max_pooling2d_27 (MaxPooling | (None, 54, 54, 32) | 0 |
| conv2d_28 (Conv2D) | (None, 52, 52, 64) | 18496 |
| activation_23 (Activation) | (None, 52, 52, 64) | 0 |
| max_pooling2d_28 (MaxPooling | (None, 26, 26, 64) | 0 |
| conv2d_29 (Conv2D) | (None, 24, 24, 128) | 73856 |
| activation_24 (Activation) | (None, 24, 24, 128) | 0 |
| max_pooling2d_29 (MaxPooling | (None, 12, 12, 128) | 0 |
| conv2d_30 (Conv2D) | (None, 10, 10, 256) | 295168 |
| max_pooling2d_30 (MaxPooling | (None, 5, 5, 256) | 0 |
| global_average_pooling2d_6 ( | (None, 256) | 0 |
| dense_8 (Dense) | (None, 3) | 771 |

Total params: 393,379

FIG. 7

SYSTEM AND METHOD FOR AUTOMATIC PERSONALIZED ASSESSMENT OF HUMAN BODY SURFACE CONDITIONS

FIELD

The present disclosure relates to assessment of human body surface conditions using image data.

BACKGROUND

The surface of the human body is the interface to the outside world, and may be viewed topologically as a taurus, including the exposed epidermis and extending to cavities such as the mouth, throat and ear. A variety of abnormal conditions on the surface of the human body exist and are commonly diagnosed via their visible presentation, including pediatric skin rashes, throat and ear infections.

Many abnormal conditions may be diagnosed via observations over the body surface, including visual and auditory information, in addition to external non-imaging information including other symptoms, onset, location on body, etc. Manual assessment from visual and auditory observations, potentially involving devices such as an otoscope or stethoscope, is time consuming and susceptible to human errors. Automated solutions exist for assessing specific conditions, however, not for diverse conditions observable across the entire body surface, including skin and cavities such as the ear and mouth, such as using mobile devices. Furthermore, automated solutions typically involve parameter estimation or training from fixed sets of generic data, and do not account for variations in image and sound data acquired from specific devices and from specific individuals.

What is therefore needed is an improved way to automatically assess medical conditions from body surface observations which address at least some of the limitations in the prior art.

SUMMARY

The present invention relates to a system and method for assessing medical conditions from image and sound data acquired from the human body surface, including generic skin rashes, ear and throat infections.

According to one broad aspect of the present invention, there is provided a system for classifying human body surface conditions from photographs, the system adapted to:
  guide a user to acquire a set of images from location of interest over the body surface, including skin, throat and ear;
  select an image from the set of images having optimal sharpness and free from motion blur;
  utilize the selected image to obtain a primary classification vector according to a number of conditions of interest including (Normal, Other, Abnormal) given the location of interest (Ear, throat, skin) via a convolutional neural network adapted and trained on image data acquired from the location of interest;
  utilize the selected image to obtain a secondary classification vector according to a number of conditions of interest given the location of interest (Ear, throat, skin) via a convolutional neural network adapted and trained on image data acquired from the location of interest;
  maintain a normal model of classification output vectors for a set of locations of interest for an individual subject acquired from healthy (Normal) body surface, and characterizing these in terms of their mean and covariance classification vectors: and
  provide a personalized diagnosis based on potentially abnormal input data, by estimating the Mahalanobis distance of the potentially abnormal output classification vector to the normal model.

In an embodiment, the system is configured to first acquire and maintain a normal baseline data map of the body surface of a specific healthy individual, including visual and auditory data observations acquired at a set of locations of interest on the body surface of a specific individual. Visual data take the form of digital video acquired from the feet, legs, torso, arms, hands, neck, face, throat, eyes, and ears, on both left and tight sides of the body, with additional hardware such as an otoscope for the ears, Auditory data take the form of microphone recordings of sounds at the mouth, front and back chest to acquire sounds from the vocal tract, heart and lungs including coughing, heartbeat and breathing, with additional hardware including a stethoscope.

Visual and auditory observations are acquired according to specific protocols at specific locations of interest and device poses relative to the body surface and according to a manual acquisition protocol ensuring minimal variability. A novel visual interface is developed to guide the user during acquisition, whereby visual targets and/or previously acquired image data are overlayed on the video acquisition view. Newly acquired visual data may be spatially aligned to the baseline data map via automatic image registration of visible landmarks including moles, wrinkles, skin texture, belly button, nipples, bony protrusions including fingers, toes, knees, elbows, shoulders, and facial landmarks. Normal baseline observations may be acquired periodically to update the body data map.

A novel system is proposed to obtain a specific and personalized prediction of the diagnosis of potentially abnormal body surface conditions, based on the output of convolutional neural network (CNN) classifiers trained to accept input image data and produce an output prediction vector. A set of hierarchical classifiers based on deep convolutional neural networks is trained to predict diagnosis from generic image data conditioned on the specific locations of interest on the body surface. Each classifier is trained to produce a prediction output vector reflecting the likelihood of a set of diagnostic labels selected according to the conditions of interest associated with the specific location of interest.

The outputs of the generic classifiers are produced across the healthy baseline map of each individual subject and used to estimate personalized models of prediction output variability in the case of healthy normal body surface conditions. After the appearance of symptoms of potentially unhealthy conditions, new data are acquired from the affected locations of interest, and the classifier outputs in response to new data are compared to the normal model in order to obtain a specific and personalized diagnosis, based on the change in classifier response for a specific subject.

In an embodiment, the system is adapted to: acquire and maintain a visual map of a subject's healthy skin composed of digital photographs, video and sound recordings acquired via a mobile camera at key locations of interest and specific poses with respect to the human body surface; selecting individual images from video having the most accurate representation of the region of interest; use the selected individual images or sound data for classifying a specific condition of interest; obtaining an initial classification vector conditional on the body location of interest from healthy data observations; and performing a second classification from suspected abnormal conditions.

Advantageously, the system provides a convenient, automatic method of diagnosing an abnormal body surface condition simply by acquiring new visual or auditory data from an individual using a mobile device capable of acquiring image and sound data, e.g., a mobile phone or other hand-held device.

In another aspect, the system provides a method of automatically assessing a differential classification by comparing data observations acquired following a suspected abnormal medical condition with data observations acquired during previous healthy baseline data map. This allows for a differential classification or diagnosis comparing the current to previous healthy interpretation of the same individual, which serves both to achieve a specific classification result and to avoid potential bias in absolute classification or diagnosis, as classification is based on data specific to the individual and acquisition device.

In another embodiment, the method comprises the protocol for acquiring a set of individual images acquired from a set of locations of interest on a human body surface map including skin, throat and ear; and sending the set of individual images to a computing system having a computer-readable medium that stores instructions, which when executed by one or more processors, cause the one or more processors to perform operations comprising: selecting an individual image from the set having an accurate representation of the body surface location of interest; generating a patient-specific classification model during normal healthy baseline conditions; predicting a personalized diagnosis from data acquired during potentially abnormal medical conditions for an individual subject and location of interest; and providing a diagnostic score based on said quantification of the abnormal medical condition.

Prior art systems have proposed diagnosing body conditions from mobile camera data, however, these methods are based on detecting and deriving metric measurements from specific body structures, such as lengths or widths of bones. In contrast, the present invention focuses on obtaining diagnosis for generic conditions of interest on the body surface such as rashes or infections which are not associated with metric measurements of specific structures but rather generic image qualities such as color and texture observable on the body surface. A wide body of literature has focused on classifying dermatological conditions using deep convolutional neural network models including conditions such as skin cancer or cosmetic facial conditions, however, these typically operate by training generic models from data of many subjects, then applying these generic trained models to predict diagnosis for new subjects, which leads to suboptimal prediction as the model is biased to the training dataset. Prediction bias may be accounted for by model calibration procedures, however, these are rarely applied to generic conditions across the body surface and are generally suboptimal for specific new unseen subjects. Systems have been designed to detect generic skin changes arising from lesions, however, they typically require specialized hardware to ensure accurate acquisition.

None of these prior art systems have proposed to integrate diverse locations of interest over the human body surface including skin, throat and ear locations, from a simple mobile camera acquisition protocol designed to reduce variability due to camera pose, to provide a personalized diagnosis based on the deviation of prediction output from a patient-specific model of healthy normal body surface.

In this respect, before explaining at least one embodiment of the invention in detail, it is to be understood that the invention is not limited in its application to the details of construction and to the arrangements of the components set forth in the following description or the examples provided therein, or illustrated in the drawings. Therefore, it will be appreciated that a number of variants and modifications can be made without departing from the teachings of the disclosure as a whole. Therefore, the present system, method and apparatus is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The present system and method will be better understood, and objects of the invention will become apparent, when consideration is given to the following detailed description thereof. Such a description refers to the annexed drawings, wherein:

FIG. 6 illustrates the generic convolutional neural network architecture used.

FIG. 7 illustrates the generic convolutional neural network architecture descriptions for skin, throat and ear locations.

Figure 1:
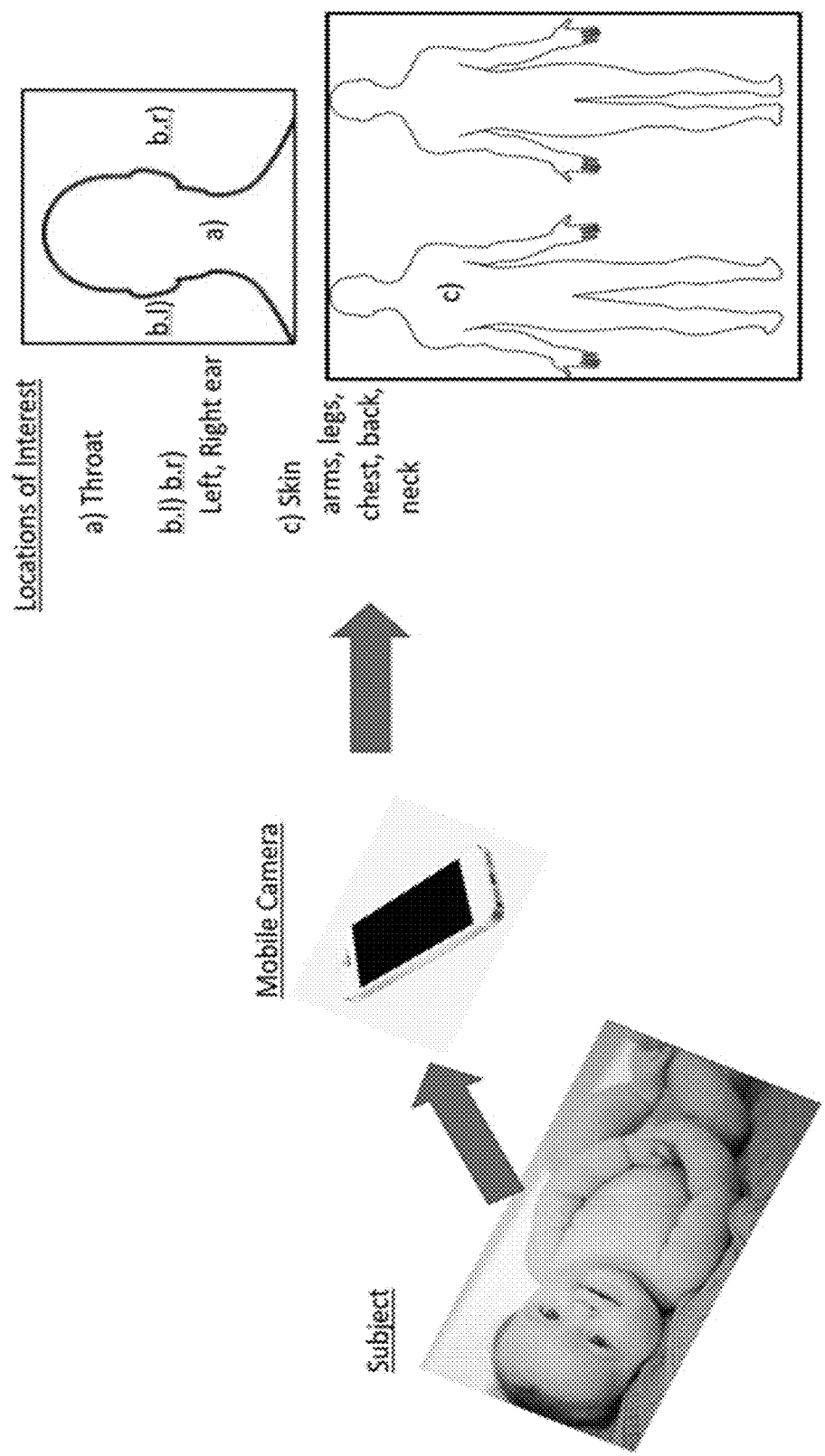
FIG. 1 shows an illustrative method in accordance with an embodiment.

Exemplary embodiments will now be described with reference to the accompanying drawings.

DETAILED DESCRIPTION OF EXEMPLARY EMBODIMENTS

Throughout the following description, specific details are set forth in order to provide a more thorough understanding to persons skilled in the art. However, well known elements may not have been shown or described in detail to avoid unnecessarily obscuring the disclosure. The following description of examples of the invention is not intended to be exhaustive or to limit the invention to the precise form of any exemplary embodiment. Accordingly, the description and drawings are to be regarded in an illustrative, rather than a restrictive, sense.

As noted above, the present invention relates to a system and method for acquiring and storing visual and auditory data over the body surface and using said data to assess abnormal conditions such as, for one non-limiting example, pediatric conditions.

More particularly, the system and method may be used to first acquire healthy baseline visual and audio data from an individual, to acquire visual and audio data under similar conditions (acquisition device, lighting, subject position relative to camera) of the same individual at the onset of suspected abnormality, and to assess potential abnormality in a personalized manner based on the difference in automatic convolutional neural network (CNN) classifier responses to healthy normal and abnormal data from the same location of interest and the same individual.

In one exemplary embodiment, there is disclosed a system for assisted acquisition of human body surface photographs acquired with a hand-held mobile phone or camera, although it will be clear to those skilled in the art that other forms of image acquisition may be used with embodiments of the present invention. A guided acquisition protocol is provided, where photos are captured from various locations of interest over the body surface, including the skin and cavities such as the mouth and the inner ear. Locations of interest are designated according to the likelihood that they will exhibit visual and/or auditory symptoms in the case of disease. A visual interface is provided in order to guide the user to the correct acquisition pose. All data are acquired with the camera light activated, in the same indoor location and lighting conditions, to minimize intensity variations between subsequent acquisitions, including initial baseline and affected acquisitions.

Video and image acquisition protocol: For each location, a short video segment of 5 seconds is acquired while the user maintains a stable camera position relative to the subject. An automatic method is used to determine a key frame image such that the photo is maximally stable and in sharp focus. The key frame image is used in subsequent differential image-based classification via convolutional neural networks. Key frame image detection is performed by maximizing the vector Laplacian operator over an input video sequence, as follows. Let $I_{xyt} \in \mathbb{R}^3$ represent a standard tricolor (red, green, blue) pixel in a video at 2D spatial location (x,y) and time t. The mathematical function used to detect the key frame is as follows:

$$D(x,y,t) = \|4I_{xyt} - I_{(x-1)yt} - I_{(x+1)yt} - I_{x(y-1)t} - I_{x(y-1)t}\| - k\|2I_{xyt} - I_{xy(t-1)} - I_{xy(t+1)}\|$$

where k is a small positive constant weighing the relative importance of spatial image sharpness vs. temporal stability. The key frame of interest is then identified as the time coordinate $t_{key}$ where the sum of D (x,y,t) over of spatial coordinates (x,y) is maximized, i.e. with high $2^{nd}$ order partial derivative magnitude across spatial locations within a single image and low $2^{nd}$ order partial derivative magnitude between frames:

$$t_{key} = \underset{t}{\mathrm{argmax}} \left\{ \sum_{x}^{Cols} \sum_{y}^{Rows} D(x, y, t) \right\}$$

Figure 2:
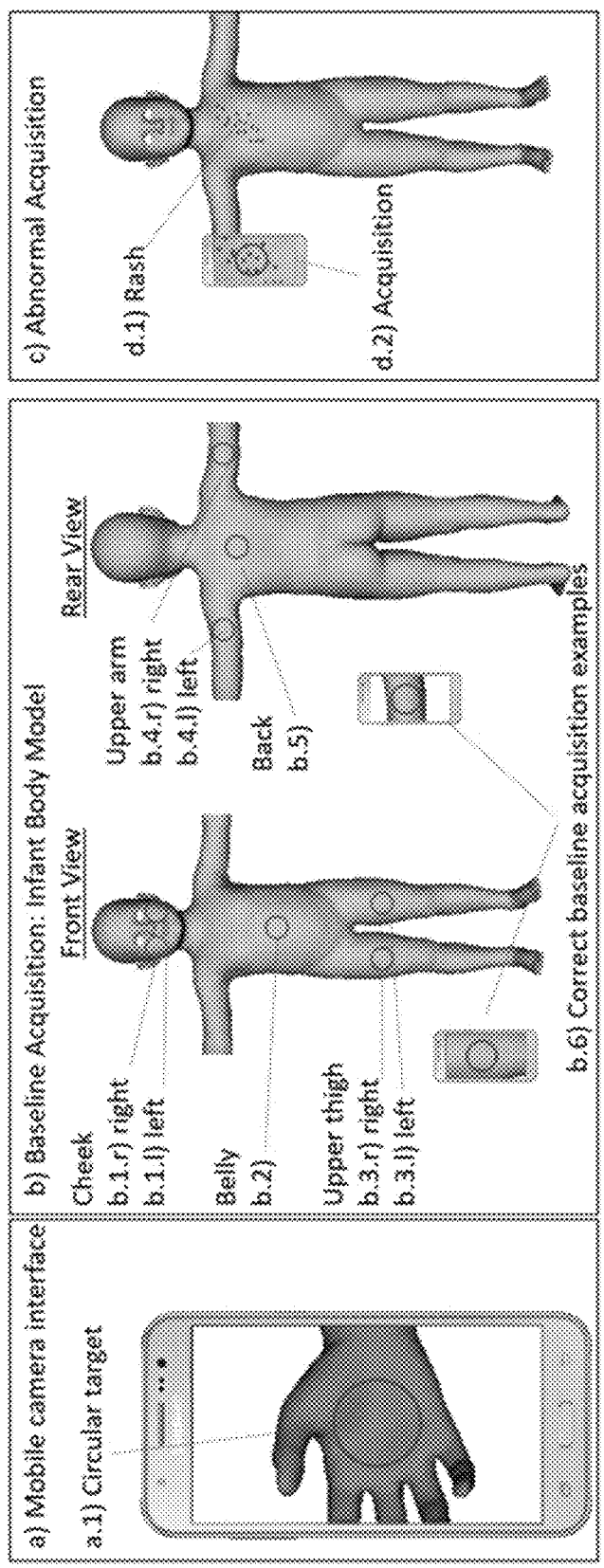
FIG. 2 illustrates the video data acquisition protocol for skin locations of interest.

Skin Data Acquisition: Skin data are acquired using a circular target superimposed upon the acquisition video interface (FIG. 2.a). The user is prompted to acquire data from an angle perpendicular to the skin surface, and at a constant distance between the camera and the skin such that the size of the circular target is approximately consistent with the target size indicated by an infant body model visualization (FIG. 2.b, FIG. 2.c), in order to ensure an approximately constant acquisition distance and pose relative to the skin surface. The circular target should fit approximately into the palm of the subject, which in the illustrated example is an infant hand (FIG. 2.a.1). Additionally, the user should ensure that the image content within the circular target contains only skin. Baseline healthy skin data are acquired from eight target locations over the body (FIG. 2.b.1 to FIG. 2.b.5), including the cheeks (left, right), the belly, the upper thigh (left, right), the upper arm (left, right) and the back. FIG. 2.b.6 shows examples of correct baseline acquisitions. In the case of an abnormal condition such as a rash, data are acquired similarly to baseline acquisition except that the circular target is positioned over the affected area such that the circular target contains only skin and the largest amount of affected skin possible (as shown in FIG. 2.d.2).

Figure 3:
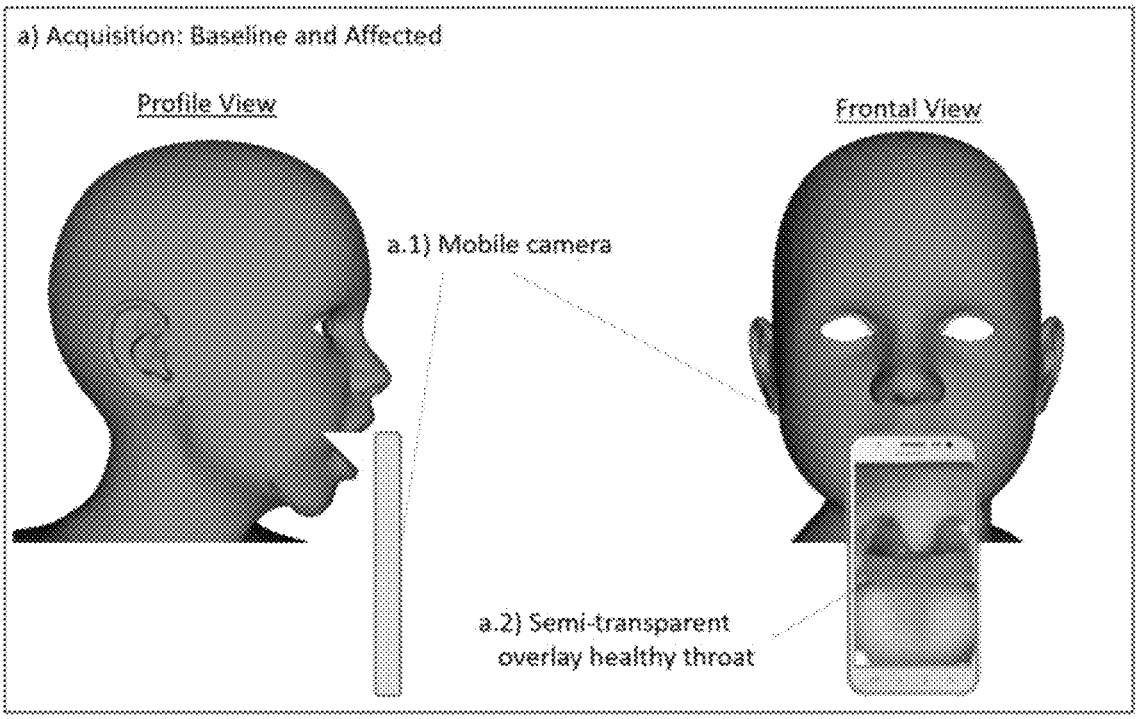
FIG. 3 illustrates the video data acquisition protocol for the throat location of interest.

Throat Data Acquisition: Data are acquired from a single throat location, with a camera positioned to face into the front of the open mouth (FIG. 3, Frontal & Profile Views). A semi-transparent overlay of a healthy throat model is used to guide the user to an optimal position vis a vis throat landmarks such as the uvula and/or the palatoglossal or palatopharyngeal arches (FIG. 3.a.2).

Figure 4:
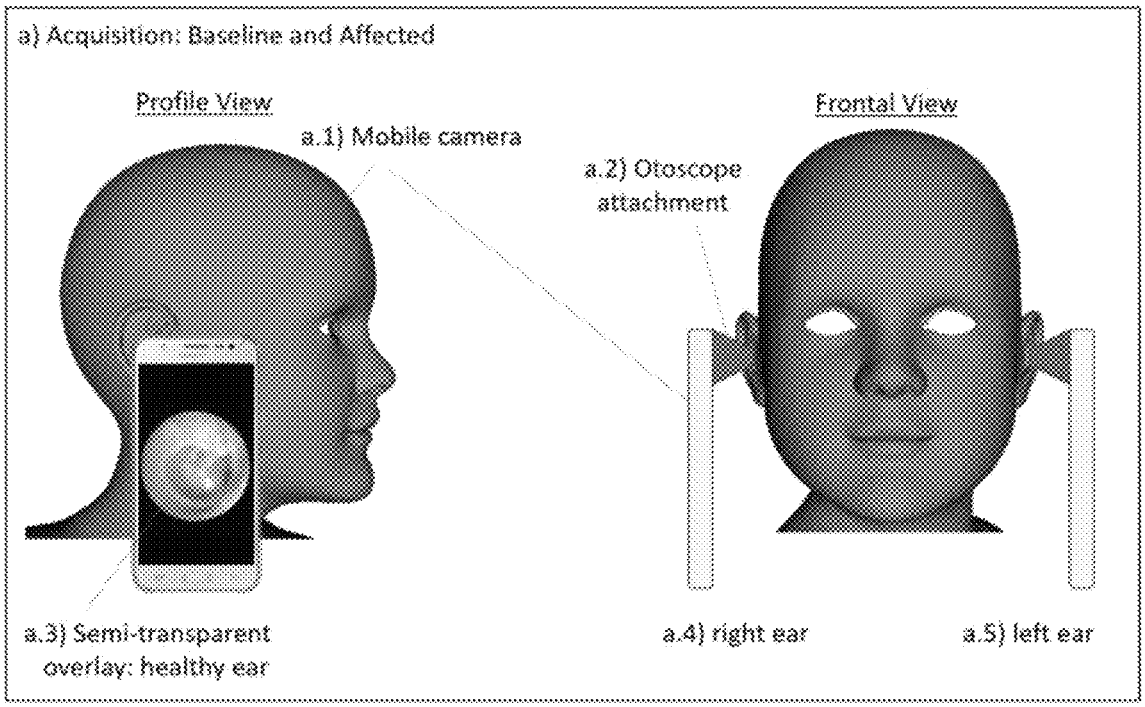
FIG. 4 illustrates the video data acquisition protocol the ear location of interest.

Ear Data Acquisition: Data are acquired from left and right ears, with a mobile camera equipped with an otoscope attachment (FIG. 4.a.2) facing into the ear (FIG. 4.a.4, 5.a.5). A semi-transparent overlay of an ear model is used to guide the user to an optimal position vis a vis ear landmarks including the incus, malleus, cone of light (FIG. 4.a.3).

In an embodiment, the system is configured to accept video data from locations of interest on the body surface, including baseline data acquired during healthy conditions and new data dud ng potentially abnormal and unhealthy conditions. Generic deep convolutional neural network (CNN) classifiers are trained to distinguish between sets of categories or labels defined according to the set of conditions at the locations of interest from preprocessed input image data I. The output vectors $\overline{C}$ of generic CNN classifiers are then modeled in order to obtain specific, unbiased and personalized diagnosis for individual patients, by comparing output vectors from healthy vs. potentially abnormal or unhealthy images of the same patient.

Figure 5:
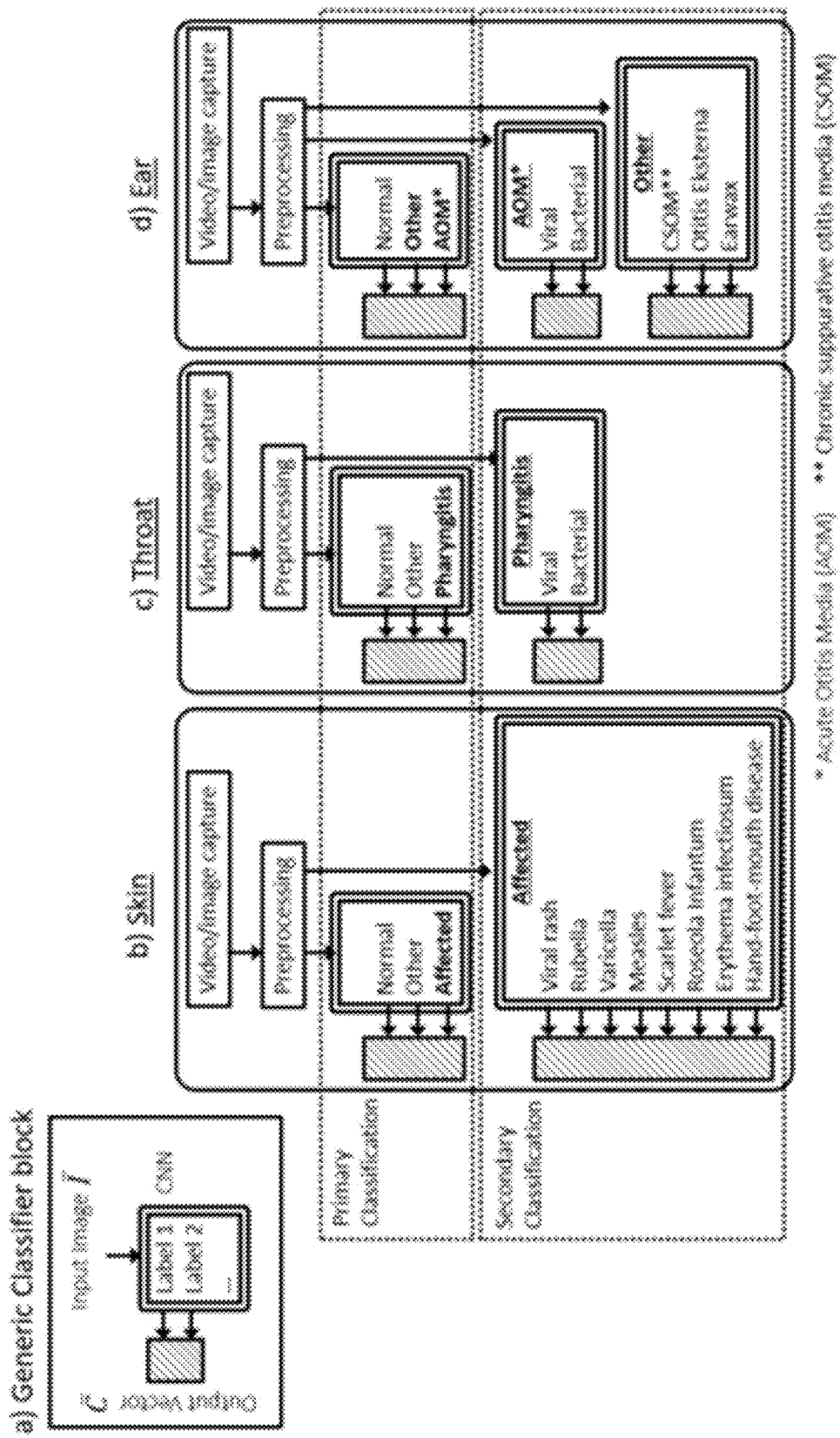
FIG. 5 illustrates the inputs and outputs of generic convolutional neural network classifiers for primary and secondary classification of labels for the skin, throat and ear locations.
Figure 8:
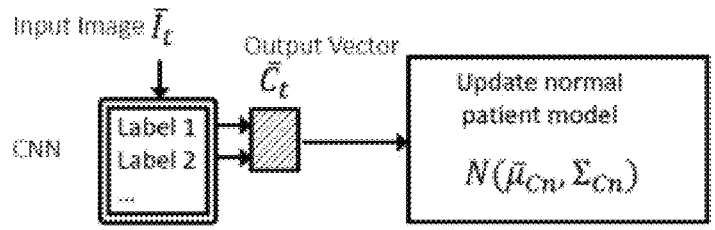
FIG. 8 illustrates the processing flow for generating a healthy normal model from healthy input image data and a generic CNN architecture.

Generic classifier: Generic classification is performed by training convolutional neural networks (CNNs) to produce an output vector $\overline{C}$ over a set of labels from a preprocessed input image $\overline{I}$ (as shown in FIG. 5 a). An output vector element $\overline{C}(i)$ represents the likelihood that the input image corresponds to the $i^{th}$ label or category. For each location of interest, one primary and one or more secondary classifiers are used based on a hierarchical set of image labels specific to the location of interest. These classifiers are trained based on images and associated ground truth labels from large sets of diverse patient data via standard CNN architectures and training algorithms, e.g., the architecture shown in FIG. 6 along with variants of the backpropagation algorithm such as stochastic gradient descent. The specific CNN architectures used may vary according to the location of interest and the output label set and are designed to maximize performance. FIG. 7 shows example architectures for skin (FIG. 7.a), throat (FIG. 7.b) and ear (FIG. 7.c).

Preprocessing: Prior to generic CNN classification, input image $\overline{I}$ is pre-processed by normalizing, including subsampling to reduce the image resolution to a fixed dimension, where the smallest dimension (width or height) is scaled, for example, to 224×224 pixels, subtracting the mean pixel value and dividing the standard deviation. An image pixel value is denoted as $I_{xy}$ and may generally be a vector-valued quantity, i.e., a tricolor pixel consisting of red, green and blue channels. The mean pixel intensity vector is defined as the sum of all pixels $I_{xy}$ divided by N:

$$\mu_I = \frac{1}{N} \sum_{x,y} I_{xy}$$

The variance is defined as the sum of the squared differences of the intensities and $$\sigma_I^2 = \frac{1}{N-1} \sum_{x,y} (I_{xy} - \mu_I)^2$$

The normalized pixel value $\hat{I}_{xy}$ following pre-processing is thus:

$$\hat{I}_{xy} = \frac{(I_{xy} - \mu_I)}{\sigma_I}$$

Hierarchical Skin Surface Classification (FIG. 5 b): The primary skin surface classifier is designed to distinguish between three categories (Normal skin, Affected, Other). The secondary classifier is designed to sub-classify the primary (Affected) skin category to distinguish between (Viral rash, Rubella, Varicella, Measles, Scarlet fever, Roseola Infantum, Erythema infectiosum, Hand-foot-mouth disease) sub-categories.

Hierarchical Throat Classification (FIG. 5 c): The primary throat classifier is designed to distinguish between three categories (Normal, Pharyngitis, Other). The secondary classifier is designed to sub-classify the primary (Pharyngitis) throat category to distinguish between (Viral, Bacterial) sub-categories.

Hierarchical Ear Classification (FIG. 5 d): The primary ear classifier is designed to distinguish between three categories (Normal, Acute Otitis Media (AOM), Other). Two independent secondary classifiers are trained to sub-classify the primary ear categories. One secondary classifier is trained to sub-classify the primary (AOM) category into (Viral, Bacterial) sub-categories. Another secondary classifier trained to sub-classify the primary (Other) category into three sub-categories (Chronic suppurative otitis media (CSOM), Otitis Eksterna, Earwax).

Individual primary and secondary classification are both based on a generic deep convolutional neural network (CNN) architecture with minor modifications as shown in FIG. 6. This is an exemplary architecture, and the present invention and methods according thereto may be used with other generic deep network architectures selectable by those skilled in the art. Following preprocessing, and input RGB image I is passed through sequential layer-wise processing steps, where standard operations at each standard layer (FIG. 6 c) generally include convolution, activation consisting of rectification (ReLu), max pooling and subsampling, by 2, and potentially a drop out layer. The second last layer-wise operation consists of spatial average pooling where each channel image is averaged over remaining (x,y) space into a single value. The last layer-wise operation is a fully connected layer where the output vector is formed as a linear combination of the result of the previous average pooling operation. A text description of the exemplary CNN architecture in FIG. 6 is provided in FIG. 6 e.

FIG. 7 provides text descriptions of the exemplary architectures used for skin (FIG. 7 a), throat (FIG. 7 b) and ear (FIG. 7 c).

The generic classifiers previously described and in previous work allow classification in an absolute sense, however, trained classifiers necessarily suffer from inductive bias towards the image data used in training, and their output classification vector will be affected by nuisances unrelated to the body surface condition of a specific individual, including the specific acquisition device (e.g., mobile phone) and the unique image appearance of a specific individual. To minimize the impact of such nuisances, the exemplary embodiment proposes a differential classification mechanism which allows a highly specific and sensitive diagnosis personalized to a specific individual.

Figure 9:
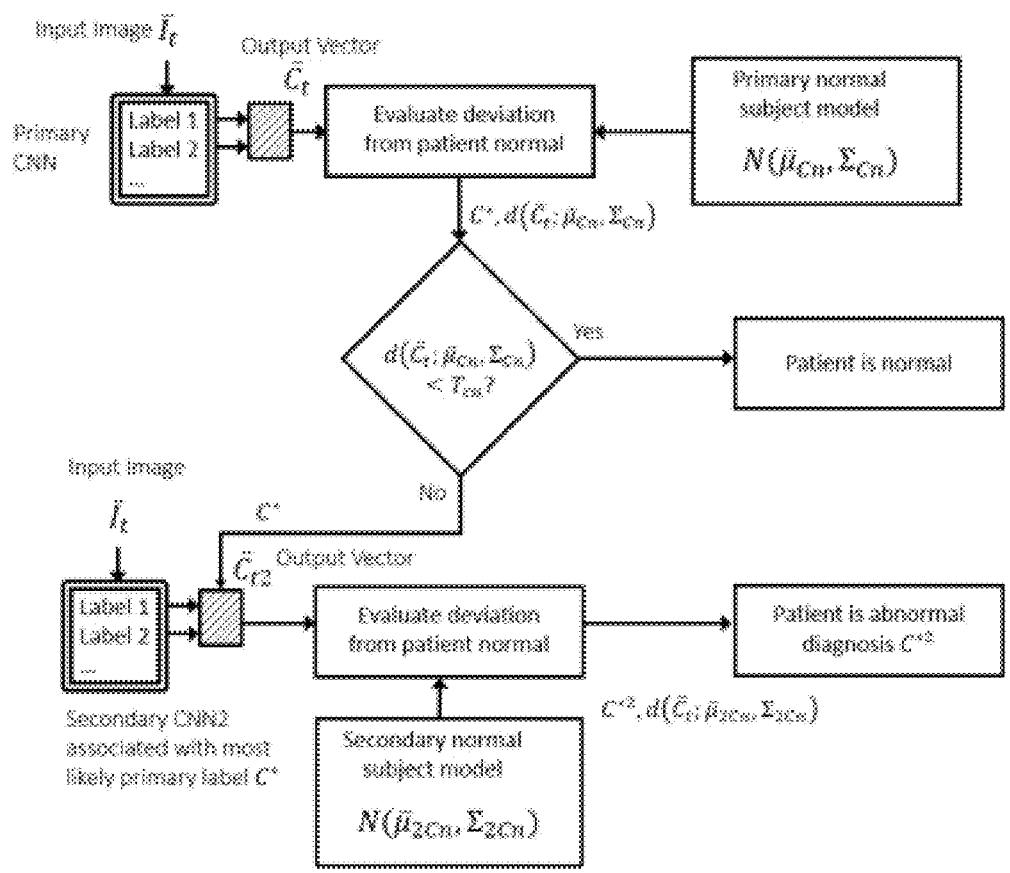
FIG. 9 illustrates the processing flow for personalized diagnosis from primary and secondary CNNs and normal patient models.

Personalized classification: Personalized classification of specific individuals operates by modeling the output vectors of generic CNN classifiers with input data from a healthy normal subject as shown in FIG. 9. Let $\bar{C}_t$ be a CNN output vector in response to an input image $\bar{I}_t$ at time t. A new user may acquire and upload multiple images at multiple time points during normal healthy conditions. Let $\bar{I}_{nt}$ represent a normal healthy image at time t at a location of interest, in which case the corresponding normal classification output vector $\bar{C}_{nt}$ is used to update a subject- and location-specific Normal density model $N(\bar{\mu}_{Cn}, \Sigma_{Cn})$ parameterized by a mean vector $\mu_{Cn}$ and covariance matrix $\Sigma_{Cn}$ estimated from the set of all normal healthy output vector data $\{\bar{C}_{nt}\}$ accumulated for the specific classifier, subject and location of interest. Mean and covariance parameters are estimated as follows:

$$\bar{\mu}_{CN} = \frac{\sum_{t=1} \alpha_t \bar{C}_{nt}}{\sum_{t=1} \alpha_t}$$

$$\Sigma_{Cn} = \frac{\sum_{t=1} \alpha_t [\bar{C}_{nt} - \bar{\mu}_{Cn}]^T [\bar{C}_{nt} - \bar{\mu}_{Cn}]}{\sum_{t=1} \alpha_t}$$

where $\alpha_t$ is a scalar weighing parameter that may be set to assign uniform weights $\alpha_t=1$ for all healthy samples $\bar{C}_{nt}$ or adjusted to provide greater emphasis on samples acquired more recently in time t. Normal subject models are computed for each primary and secondary CNN.

Once a normal subject model $N(\bar{\mu}_{Cn}, \Sigma_{Cn})$ has been generated for a CNN, the Mahalanobis distance may be used to compute the deviation of a new classification vector $\bar{C}_t$ from the normal model. The Mahalanobis distance $d(\bar{C}_t; \bar{\mu}_{Cn}, \Sigma_{Cn})$ is defined according to the vector difference $\bar{C}_t - \bar{\mu}_{Cn}$ between a new classification output vector $\bar{C}_t$ and the normal mean vector $\bar{\mu}_{Cn}$ as follows:

$$d\left(\bar{C}_t; \bar{\mu}_{Cn}, \sum\nolimits_{Cn}\right) = \sqrt{[\bar{C}_t - \bar{\mu}_{Cn}]^T \sum\nolimits_{Cn}^{-1} [\bar{C}_t - \bar{\mu}_{Cn}]}$$

The Mahalanobis distance reflects the likelihood that a classification output vector $\bar{C}_t$ deviates from the patient-specific normal density, and serves as a personalized diagnostic measure that may be compared against a threshold $T_{cn}$ to predict whether a specific patient is normal or abnormal. The specific threshold $T_{cn}$ may be determined according to a desired statistical cutoff value for a. CNN based on the associated covariance matrix $\Sigma_{Cn}$, e.g., according to a number of standard deviations.

Personalized diagnosis is performed in the case where an input image $I_t$ is acquired from a potentially abnormal body surface condition for a specific patient and location of interest, and proceeds according to the flowchart shown in FIG. 9 and as described herein. The primary classification output vector $\overline{C}_t$ is first produced from the input image $I_t$ and the appropriate primary CNN trained from primary labels (e.g., Normal, Other, Affected). If the Mahalanobis distance is less than the threshold $d(\overline{C}_t; \overline{\mu}_{Cn}, \Sigma_{Cn}) \geq T_{cn}$, then the patient is deemed to be normal.

If the Mahalanobis distance is greater or equal to the threshold $d(\overline{C}_t; \overline{\mu}_{Cn}, \Sigma_{Cn}) \geq T_{cn}$, then the patient is deemed to be not normal. The most likely primary classification label C* other than normal is determined as the label i maximizing the absolute difference $|\overline{C}_t(i) - \overline{\mu}_{Cn}(i)|$ divided by the standard deviation $\sqrt{\Sigma_{Cn}(i,i)}$ of the normal covariance matrix as follows:

$$C^* = \operatorname*{argmax}_i \left\{ \frac{|\overline{C}_t(i) - \overline{\mu}_{Cn}(i)|}{\sqrt{\Sigma_{Cn}(i,i)}} \right\}$$

Given this determined from the primary classification label C*, a secondary output vector $\overline{C}_{t2}$ is then computed from the appropriate secondary CNN2. The secondary classification label $C^{*2}$ is determined from a secondary normal density model $N(\overline{\mu}_{C2n}, \Sigma_{C2n})$ associated with CNN2 as the label i maximizing the absolute difference $|\overline{C}_{t2}(i) - \overline{\mu}_{C2n}(i)|$ divided by the standard deviation $\sqrt{\Sigma_{C2n}(i,i)}$ of the normal covariance matrix as follows $$C^{*2} = \operatorname*{argmax}_i \left\{ \frac{|\overline{C}_{2t}(i) - \overline{\mu}_{C2n}(i)|}{\sqrt{\Sigma_{C2n}(i,i)}} \right\}$$

Finally, the Mahalanobis distance $d(\overline{C}_{t2}; \overline{\mu}_{C2n}, \Sigma_{C2n})$ may be used to provide an estimate of the statistical significance of the secondary classification.

Advantageously, exemplary systems according to the present invention may provide a convenient and accurate way to provide a personalized diagnosis of potentially abnormal conditions from an image of a subject's body surface acquired via a mobile phone or other hand-held device.

In this illustrative embodiment, data is acquired remotely via standard mobile phone technology, for example, an iPhone™ acquiring an image at 2448 pixels*3264 pixels or another suitable resolution. No additional hardware is needed. Basically, the picture could be captured using any device embedding a camera, including (the following is non-exhaustive):

smart phones, or mobile phones embedding a camera
tablet computers
hand-held digital cameras In an embodiment, a specialized acquisition view is provided and used to guide the user in acquiring the image. After acquisition, all image data are uploaded to a central server for subsequent processing.

Figure 10:
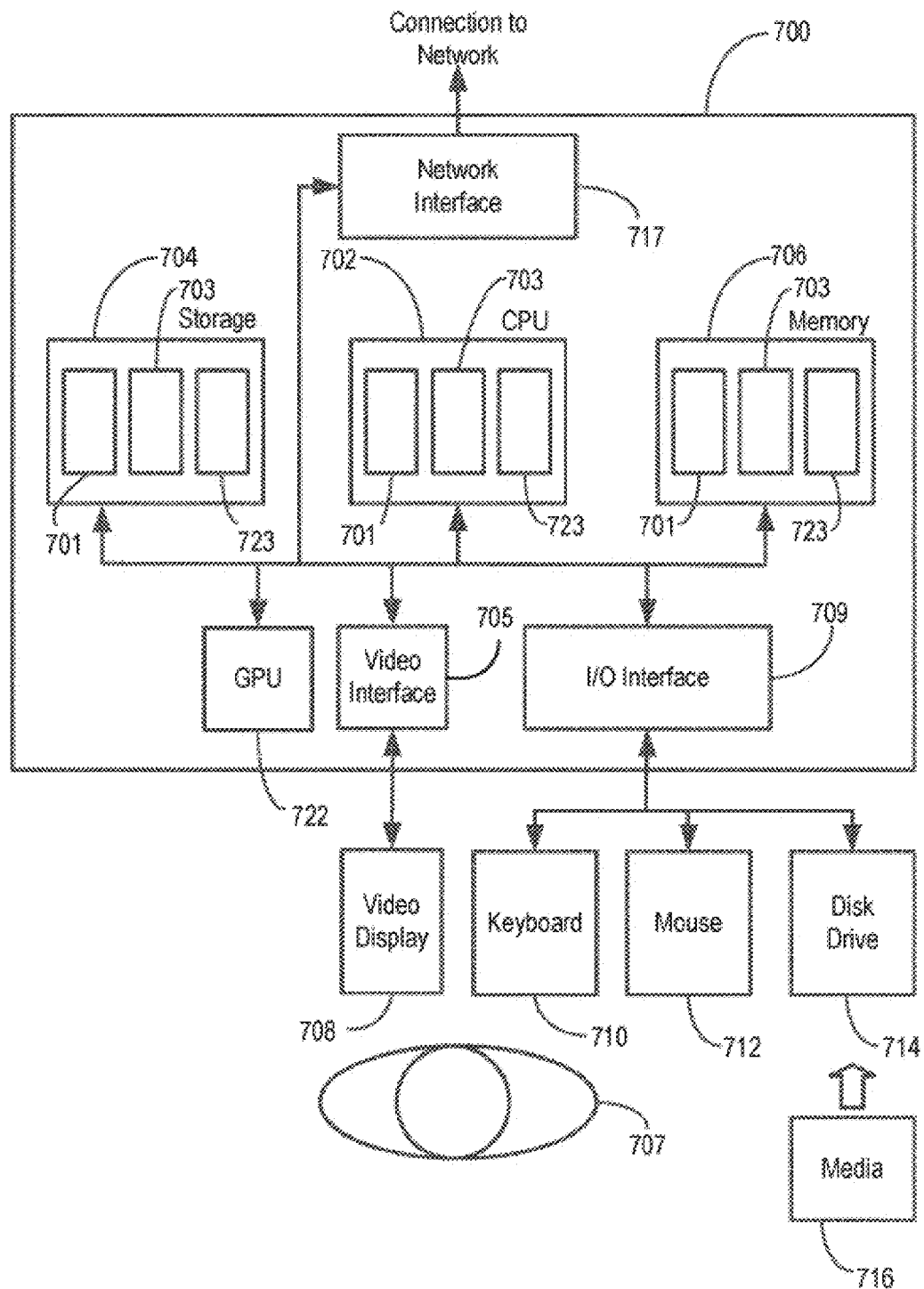
FIG. 10 illustrates a schematic block diagram of a computing device in accordance with an embodiment of the present invention.

Now referring to FIG. 10, a schematic block diagram of a computing device is illustrated that may provide a suitable operating environment in one or more embodiments. A suitably configured computer device, and associated communications networks, devices, software and firmware may provide a platform for enabling one or more embodiments as described above. By way of example, FIG. 10 shows a computer device 700 that may include a central processing unit ("CPU") 702 connected to a storage unit 704 and to a random access memory 706. The CPU 702 may process an operating system 701, application program 703, and data 723. The operating system 701, application program 703, and data 723 may be stored in storage unit 704 and loaded into memory 706, as may be required. Computer device 700 may further include a graphics processing unit (GPU) 722 which is operatively connected to CPU 702 and to memory 706 to offload intensive image processing calculations from CPU 702 and run these calculations in parallel with CPU 702. An operator 707 may interact with the computer device 700 using a video display 708 connected by a video interface 705, and various input/output devices such as a keyboard 710, pointer 712, and storage 714 connected by an I/O interface 709. In known manner, the pointer 712 may be configured to control movement of a cursor or pointer icon in the video display 708, and to operate various graphical user interface (GUI) controls appearing in the video display 708. The computer device 700 may form part of a network via a network interface 717, allowing the computer device 700 to communicate with other suitably configured data processing systems or circuits. A non-transitory medium 716 may be used to store executable code embodying one or more embodiments of the present method on the computing device 700.

The foregoing is considered as illustrative only of the principles of the present invention. The scope of the claims should not be limited by the exemplary embodiments set forth in the foregoing, but should be given the broadest interpretation consistent with the specification as a whole.

The invention claimed is:

1. A system for identifying an abnormal human body surface condition from image data, the system adapted to:
   guide a user to acquire at least one first image from at least one location of interest on a body surface of an individual subject when the individual subject is in a normal healthy condition;
   a mobile data capture device for use by the user in acquiring the at least one first image under data acquisition criteria to standardize data acquisition, the at least one location of interest selected from skin, throat and ear, and the data acquisition criteria comprising a set distance and relative orientation between the mobile data capture device and the at least one location of interest during data capture;
   utilize the at least one first image to obtain a first classification vector according to a number of conditions of interest given the at least one location of interest via a convolutional neural network trained on image data acquired from at least one same location of interest;
   maintain a normal model of classification output vectors for the at least one location of interest for the individual subject acquired under the normal healthy condition, the normal model parameterized by a mean vector and covariance matrix;
   utilize at least one second image of the at least one location of interest on the individual subject acquired under the data acquisition criteria subsequent to the acquisition of the first image, the at least one second image defined by a second classification vector obtained via the convolutional neural network;
   estimate a Mahalanobis distance between the mean vector and the second classification vectors;
   compare the Mahalanobis distance against a set threshold indicative of abnormal unhealthy skin condition of the individual subject; and if the Mahalanobis distance is above the set threshold outputting an indication of the abnormal human body surface condition for the individual subject.

2. The system of claim 1 wherein acquiring the at least one first image comprises acquiring first video data and selecting the at least one first image from the first video data on the basis of optimal sharpness and freedom from motion blur to train the convolutional neural network, and acquiring the at least one second image comprises acquiring second video data and selecting the at least one second image from the second video data on the basis of optimal sharpness and freedom from motion blur.

3. The system of claim 1 wherein the mobile data capture device comprises a visual user interface, wherein the data acquisition criteria comprise a semi-transparent visual guide displayable on the visual user interface spatially alignable to the at least one location of interest.

4. The system of claim 1 wherein the first image comprises a plurality of images of the at least one location of interest on the individual subject to train the convolutional neural network.

5. A method for obtaining an indication of an abnormal human body surface condition for an individual subject using a mobile data capture device, comprising the steps of:
  a. selecting at least one location of interest on a body surface of the individual subject;
  b. establishing data acquisition criteria to standardize data acquisition, the data acquisition criteria comprising (i) a set distance and relative orientation between the mobile data capture device and the at least one location of interest during data capture;
  c. using the mobile data capture device under the data acquisition criteria to acquire first image data for the at least one location of interest when the individual subject is in a normal healthy condition;
  d. establishing a normal baseline surface condition for the at least one location of interest for the individual subject, the normal baseline condition defined by at least one first classification vector obtained via a convolutional neural network using the first image data;
  e. subsequent to step d., using the mobile data capture device under the data acquisition criteria to acquire second image data of the at least one location of interest, the second image data defined by at least one second classification vector obtained via the convolutional neural network;
  f. computing a deviation of the at least one second classification vector from a normal model generated from the at least one first classification vector by estimating a Mahalanobis distance; and
  g. wherein when the Mahalanobis distance is above a set threshold, outputting an indication of the abnormal human body surface condition being present for the individual subject.

6. The method of claim 5 wherein the step of acquiring the first image data comprises acquiring first video data and selecting a first image from the first video data on the basis of optimal sharpness and freedom from motion blur to train the convolutional neural network, and acquiring the second image data comprises acquiring second video data and selecting a second image from the second video data on the basis of optimal sharpness and freedom from motion blur.

7. The method of claim 5 wherein the at least one location of interest is selected from skin and body cavity surface.

8. The method of claim 5 wherein the data acquisition criteria comprise a semi-transparent visual guide displayable on a user interface of the mobile data capture device spatially alignable to the at least one location of interest.

9. The method of claim 5 wherein the first image data comprises a plurality of image data to train the convolutional neural network.

\* \* \* \* \*